United States Patent [19]
Rao et al.

[11] Patent Number: 5,412,123
[45] Date of Patent: May 2, 1995

[54] ANTHRAQUINONE AND ANTHRACENE DERIVATIVES AS INHIBITORS OF THE CELL-ADHESION MOLECULES OF THE IMMUNE SYSTEM

[75] Inventors: Narasinga Rao, Alameda; Peng C. Tang, Moraga; John H. Musser, San Carlos, all of Calif.

[73] Assignee: Glycomed Incorporated, Alameda, Calif.

[21] Appl. No.: 14,913

[22] Filed: Feb. 8, 1993

[51] Int. Cl.$^6$ .............................................. C07D 315/00
[52] U.S. Cl. .................................... 552/209; 552/234; 552/236; 552/240; 552/242; 552/243; 552/262; 549/426; 549/427
[58] Field of Search ............... 552/209, 234, 236, 240, 552/242, 243, 262; 549/426, 427

[56] References Cited
U.S. PATENT DOCUMENTS 4,849,513  7/1989  Smith et al. ............................ 536/27
5,143,712  9/1992  Brandley et al. ...................... 424/1.1

FOREIGN PATENT DOCUMENTS

WO90/09435   8/1990   WIPO.
WO90/13300  11/1990   WIPO.
WO91/15200  10/1991   WIPO.

OTHER PUBLICATIONS

Article by Ames, et al., published by *Synthesis*, 364 (1981).
Article by Cameron et al., entitled "Chemistry of the Coccoidea. VIII Synthesis of the Ancient Dyestuff Kermesic Acid and of Related Anthraquinones" published by *Aust. J. Chem.*, (1981) 34:2401–21.
Article by Dodd et al., entitled "Lactoseries Carbohydrates Specify Subsets of Dorsal Root Ganglion Neurons Projecting to the Superficial Dorsal Horn of Rat Spinal Cord" published by *J. Neurosci.*, (1985) 5:3278–3294.
Article by Kraus entitled "An Improved Reductive Methylation Procedure for Quinones" published by *Synthetic Communication*, (1986) 16(9):1037–1042.
Article by Nagoioka et al., published by *Tetra. Lett.*, 22, 899 (81).
Article by McOmie et al., entitled "The Thiele-Winter Acetoxylation of Quinones" published by *Organic Reactions*, (1960) 19:199.
Article by Cai et al., entitled "Stereoselective and Mild Method for the Synthesis of C-D-glucosylarenes in High Yield" published by *Carbohydrate Res.*, Elsevier Science Publishers B.V., (1989) 191:125–129.
Article by Dimroth et al., entitled "Berichte der Deutschen Chemischen Gesellschaft" published by *Berlchte d. D. Chem.*, (1920) 471–480.
Article by Allevi et al., entitled "The First Direct Method of C-Glucopyranosyl Derivatization of 2,3,4,6-Tetra-O-benzyl-D-glucopyranose" published by *J. Chem. Soc.*, Chem. Comm. (1987) 1245–1246.
Article by Allevi et al, entitled "The First Total Synthesis of Carminic Acid" published by *J. Chem. Soc.*, Chem. Comm. (1991) 1319–1320.
Article by Austin et al, published by *J. Chem. Soc.*, Chem. Comm. (1964) 2128.
Article by Czernecki et al., entitled "Stereospecific C-Glycosylation of Aromatic and Heterocyclic Rings" published by *J. Org. Chem.* (1989) 54:610.
Article by Takahashi et al, published by *Synthesis*, (1980) 627.

*Primary Examiner*—Paul J. Killos
*Attorney, Agent, or Firm*—Gregory J. Giotta

[57] ABSTRACT

Derivatives of anthraquinone and anthracene are synthesized and formulated into pharmaceutical formulations. When the formulations are administered the derivatives act as ligands binding to an interrupting the biological chain of events associated with selectin receptors in the human body.

17 Claims, 3 Drawing Sheets

ANTHRAQUINONE AND ANTHRACENE DERIVATIVES AS INHIBITORS OF THE CELL-ADHESION MOLECULES OF THE IMMUNE SYSTEM

FIELD OF THE INVENTION

This invention relates generally to determining the presence of and relieving the effects of certain diseases, which effects are attributed to cell—cell adhesions. More specifically, this invention relates to the administration of pharmaceutical formulations containing derivatives of anthraquinone and/or anthracene in amounts sufficient to inhibit E-, L- and P-selectins present on cellular surfaces and thereby prevent and/or alleviate the effects of diseases such as relieving the inflammation caused by autoimmune diseases such as arthritis, psoriasis and multiple sclerosis.

BACKGROUND OF THE INVENTION

While protein—protein interactions in cell recognition have been recognized for some time, only recently has the role of carbohydrates in physiologically relevant recognition been widely considered (see Brandley, B. K., and Schnaar, R. L., *J. Leuk. Biol.* (1986) 40:97; and Sharon, N., and Lis, H., *Science* (1989) 246:227). Oligosaccharides are well positioned to act as recognition molecules due to their cell surface location and structural diversity. Many oligosaccharide structures can be created through the differential activities of a smaller number of glycosyltransferases. Their diverse structures, then, can be generated with relatively few gene products, suggesting a plausible mechanism for establishing the information necessary to direct a wide range of cell—cell interactions. Examples of differential expression of cell surface carbohydrates and putative carbohydrate binding proteins (lectins) on interacting cells have been described (see Dodd, J., and Jessel, T. M., *J. Neurosci.* (1985) 5:3278; Regan, L. J., et al., *Proc. Natl. Acad. Sci. USA* (1986) 83:2248; Constantine-Paton M., et al., *Nature* (1986) 324:459; and Tiemeyer, M., et al., *J. Biol. Chem.* (1989) 263:1671). Further, the question has been raised as to the nature of the leukocyte receptor for ELAM-1 (see Bevilacqua et al. *Proc Natl. Acad. Sci. USA* (1987) 84:9238).

Tumor associated glycolipids have been reported in fetal tissue and a variety of human cancers, including CML cells (Fukuda, M. N., et al., *J. Biol. Chem.* (1986) 261:2376; Magnani, J. L., et al., *J. Biol. Chem.* (1982) 257:14365; Hakomori, S., et al., *Biochem. Biophys. Res. Comm.* (1983) 113:791). This has led to the hypothesis that these structures may be important in many developmental and oncogenic processes (J. L. Magnani et al., J. Biol. Chem. (1982) 257:14365). Smaller quantities of most of these carbohydrates can be found in normal human tissue (see Fukushi, Y., et al., *J. Exp. Med.* (1984) 160:506), but until now no function for these structures has been reported.

Adhesion of circulating neutrophils to stimulated vascular endothelium is a primary event of the inflammatory response. Several receptors have been implicated in this interaction, including a family of putative lectins that includes gp90$^{MEL}$ (Leu8), GMP-140 (PADGEM) and ELAM-1 (Gong, J.-G., et al., *Nature* (1990) 343:757; Johnston, G. I., et al., *Cell* (1989) 56:1033; Geoffrey, J. S., and Rosen, S. D., *J. Cell Biol.* (1989) 109:2463; Lasky, L. A., et al., *Cell* (1989) 56:1045). These receptors each contain a domain with sequence homology to calcium dependent lectins, and gp90$^{MEL}$ has been demonstrated to recognize a carbohydrate (see J. S. Geoffrey et al., *J Cell Biol.* (1989) 109:2463). Endogenous ligands for these receptors are beginning to be characterized (see U.S. Pat. No. 5,143,712 issued Sep. 1, 1992, incorporated herein by reference).

One receptor referred to as E- selectin or ELAM-1 provides transient expression on endothelial cells in response to IL-1 or TNF (Bevilacqua, M. P., et al., *Science* (1989) 243:1160). The time course of this induced expression (2–8 h) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding for the ELAM-1 receptor.

Recently, several different groups have published papers regarding ELAM-1 ligands which ligands are also referred to as LECAM-2 ligands. Lowe et al. (1990) demonstrated a positive correlation between the LECAM-2 dependent adhesion of HL-60 cell variants and transfected cell lines, with their expression of the sialyl Lewis x (sLex) oligosaccharide, Neu NAc α2-3Gal-β1-4(Fuc α1-3)-GlcNAc. By transfecting cells with plasmids containing an α(1,3/1,4) fucosyltransferase, they were able to convert non-myeloid COS or CHO lines into sLex-positive cells that bind in an LECAM-2 dependent manner. Attempts to block LECAM-2 dependent adhesion using anti-sLex antibodies were uninterpretable due to the agglutination of the test cells by the antibody. They conclude that one or more members of a family of oligosaccharides consisting of sialylated, fucosylated, lactosaminoglycans are the ligands for the lectin domain of LECAM-2. Phillips et al. (1990) used antibodies with reported specificity for sLex to inhibit the LECAM-2 dependent adhesion of HL-60 or LEC11 CHO cells to activated endothelial cells. Liposomes containing difucosylated glycolipids with terminal sLex structures inhibited adhesion, while those containing nonsialylated Lex structures were partially inhibitory. Walz et al. (1990) were able to inhibit the binding of a LECAM-2-1gG chimera to HL-60 cells with a monoclonal antibody directed against sLex or by glycoproteins with the sLex structure, but could not demonstrate inhibition with CD65 or CD15 antibodies. Both groups concluded that the sLex structure is the ligand for LECAM-2.

LECAM-1 is particularly interesting because of its ability to block neutrophil influx (Watson et al., *Nature* (1991) 349:164–167). It was expressed in chronic lymphocytic leukemia cells which bind to HEV (see Spertini et al., *Nature* (1991) 349:691–694). It is believed that HEV structures at sites of chronic inflammation are associated with the symptoms of disease such as rheumatoid arthritis, psoriasis, and multiple sclerosis.

Information regarding the DNA sequences encoding endothelial cell-leukocyte adhesion molecules are disclosed in PCT published application WO90/13300 published November 15, 1990 incorporated herein by reference. The PCT publication cites numerous articles which may be related to endothelial cell-leukocyte adhesion molecules. The PCT publication claims methods of identifying ELAM-ligands, as well as methods of inhibiting adhesion between leukocytes and endothelial cells using such ligands and specifically refers to MILAs which are described as molecules involved in leukocyte adhesion to endothelial cells.

In general, the above publications are directed toward identifying and characterizing endogenous ligands which are believed to be carbohydrates. The present invention is directed toward synthetic compounds which act as agonists or antagonists of naturally occurring ligands.

SUMMARY OF THE INVENTION

Derivatives of anthraquinone and anthracene are synthesized and formulated into pharmaceutical formulations. When the formulations are administered the derivatives act as ligands binding to an interrupting the biological chain of events associated with selectin receptors in the human body. By blocking selectin receptors it is possible to alleviate the effects of and thereby treat a wide range of diseases and abnormal conditions.

Antagonist ligand molecules act as biochemical blocking agents by binding to selectins (such as ELAM-1 and LECAM-1) and preventing circulating neutrophils from binding to stimulated endothelial cells, thereby preventing a primary event of the inflammatory response. Agonist ligands have the opposite effect, i.e., they act in the same manner as and/or enhance the effects of endogenous ligands. The ligands of the invention are of the formula I:

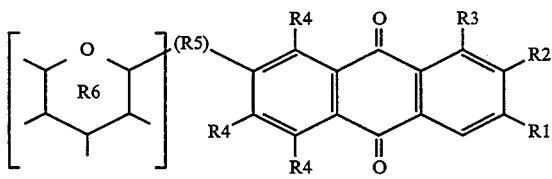

R1=OH, O-alkyl wherein the alkyl contains 1 to 6 carbon atoms, or O-linker wherein the linker group is an alkyl containing 1 to 12 carbon atoms or a heteroalkyl containing 1 to 12 atoms which contains heteroatoms selected from the group consisting of S, N, and O.

R2=R—COOH, or $CH_2$—O—$CO_2H$, $CH_2O$—R—$CO_2H$, $OCH_2CO_2H$, O—R—O—$SO_3$, O—R—O—$PO_3$ or O—R—$CO_2H$ wherein R is an alkyl containing 1 to 6 carbon atoms;

R3=H, an alkyl containing 1 to 6 carbon atoms or a heteroalkyl containing 1 to 6 atoms with the heteroatom being selected from the group consisting of N, S, and O;

R4=OH, or O—R' wherein R' is an alkyl containing 1 to 6 carbon atoms or a heteroalkyl containing 1 to 6 atoms with the heteroatom being selected from the group consisting of S and N;

R5=—$(CH_2)_n$— wherein n is an integer of from 1 to 12 and the —$(CH_2)_n$— group may be further attached to a heteroatom selected from the group consisting of N, S and O; and R6=Hexose or a hexNAc, or a disaccharide linked by either α- or β-linkage to R5 through a linking group which includes as a base atom chain comprised of atoms selected from the group consisting of C, O, N and S such that the linking group may be, —O—, or —$(CH_2)$—$_n$ wherein n is an integer of from 1 to 6.

In addition, the invention includes pharmaceutically acceptable salts of compounds of formula I and multivalent derivatives thereof.

These ligands can be bound (such as by the linker of R1) to anti-inflammatory drugs and/or formulated to provide, for example, compositions useful in assaying a sample for the presence of selectins such as E-, L- and P-selectins, compositions useful in detecting the site of inflammation in a patient, or pharmaceutical compositions useful in treating acute inflammation (or treating the inflammatory symptoms of certain diseases) or affecting other phenomena involving cell-to-cell interactions such as the interaction of ELAM-1 on endothelial cells and/or LECAM-1 on circulating neutrophils.

An important aspect of the invention is pharmaceutical compositions which are useful in treating, preventing and/or alleviating any undesirable effects resulting from cell—cell interactions and specifically those involving E-, L-, and P-selectins, e.g., the interaction of ELAM-1 receptors and circulating neutrophils and/or LECAM-1 receptors and endothelial cells. Such compositions are comprised of an inactive ingredient in the form of a pharmaceutically acceptable excipient carrier material and at least one ligand capable of effectively binding to a selectin receptor.

A primary object of the invention is to provide a synthetic selectin ligand in a useful formulation, preferably a pharmaceutical formulation.

Another object is to provide a composition comprising a synthetic L-, E-, or P-selectin ligand which is preferably labeled and which can be used to assay for the presence of L-, E-, or P-selectins in a sample.

Another object is to provide a pharmaceutical formulation containing a derivative of anthraquinone or anthracene which functions as a selectin ligand which is useful in treating inflammation.

Yet another object of the invention is to provide pharmaceutical formulations containing multivalent derivatives of formula I or related multivalent derivatives, preferably multivalent derivatives of sennoside A or sennoside B.

Other objects include providing methods to treat inflammation and to determine the site of inflammation by administering formulations of the type referred to above.

An advantage of the invention is that the ligands are non-toxic compounds with particular functional groups and three-dimensional configurations which allow them to bind selectin receptors effectively and thereby block neutrophils binding to the receptors in numbers per unit of time which result in inflammation and/or other adverse effects.

A feature of the present invention is that the ligands can be labeled and the labeled ligand used in an assay to detect the presence of selectins in a sample.

Other features of the invention include the ability of pharmaceutical formulations of the invention to relieve the inflammatory symptoms of a wide range of diseases which are characterized by the binding of excessive amounts of neutrophils to a site, i.e., an ELAM-1 receptor site.

These and other objects, advantages and features of the present invention will become apparent to those persons skilled in the art upon reading the details of the structure, synthesis, formulation and usage as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows.

DETAILED DESCRIPTION OF PREFERRED EMBODIMENTS

Before the present derivatives of anthraquinone and anthracine which act as ligands and composition containing such ligands and processes for synthesizing, formulating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

As used in this specification and the appended claims, the singular forms "a", "an" and "the" include plural referents unless the context clearly dictates otherwise. Thus, for example, reference to "a ligand" includes mixtures of ligands, reference to "an anthraquinone derivative" includes reference to mixtures of such molecules, reference to "the formulation" or "the method" includes one or more formulations, methods and/or steps of the type described herein and/or which will become apparent to those persons skilled in the art upon reading this disclosure and so forth.

Some standard abbreviations used in connection with the present invention include: BSA, bovine serum albumin; DEAE, diethylaminoethyl; DMSO, dimethylsulfoxide; ELAM-1, or E-selectin endothelial/leukocyte adhesion molecule-1; HPTLC, high performance thin layer chroma-tography; LECAM-1, or L-selectin leukocyte/endothelial cell adhesion molecule-1; MOPS, 3-[N-Morpholino]propanesulfonic acid; NANA, N-acetylneuraminic acid; PVC, polyvinylchloride; TLC, thin layer chromatography; TFA, trifluoroacetic acid; Tris, Iris (hydroxymethyl) aminomethane.

A. General Overview

Figure 1:
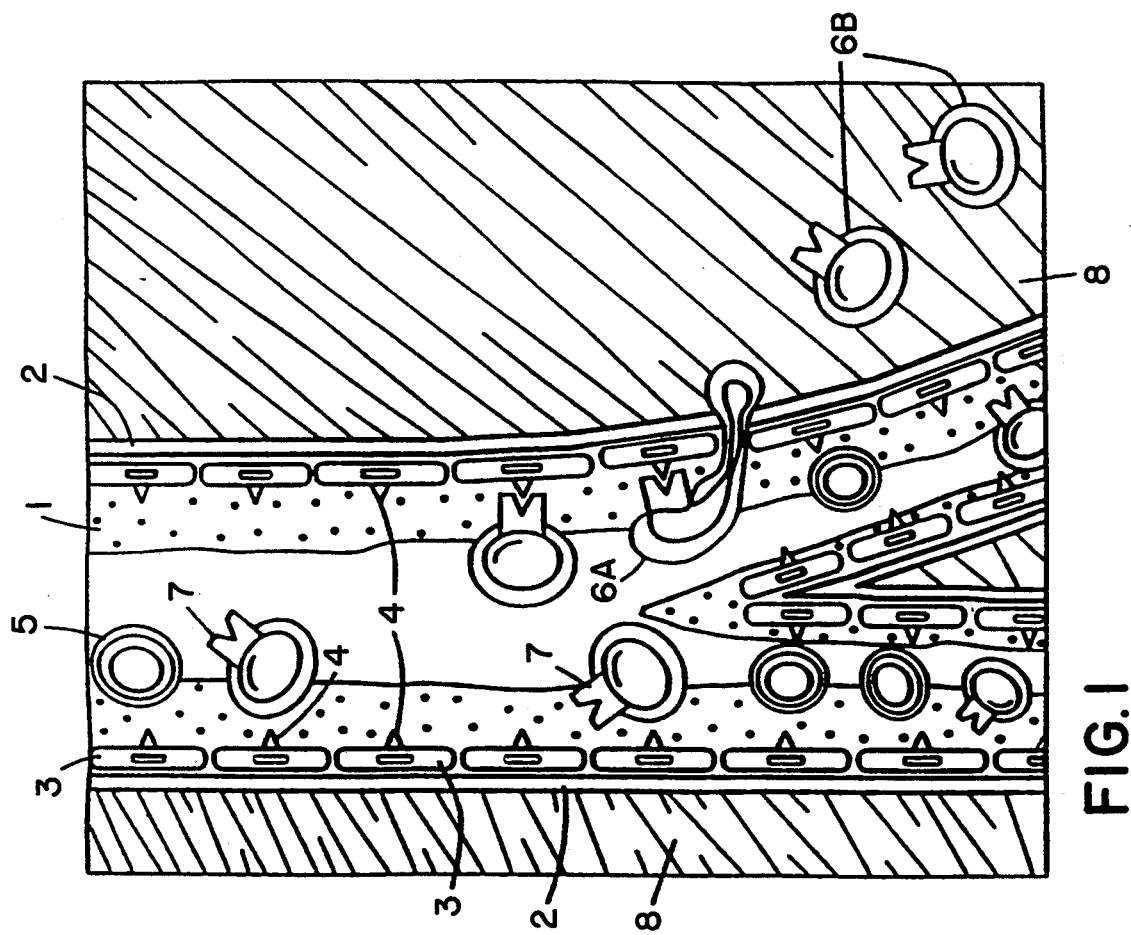
FIG. 1 is a cross-sectional schematic view showing the interaction between white blood cells and activated endothelial cells.

Referring now to FIG. 1, a cross-sectional view of a blood vessel 1 is shown. The vessel wall 2 is lined internally with endothelial cells 3. The endothelial cells 3 can be activated causing the cells 3 to synthesize ELAM-1 which is displayed in FIG. 1 as a triangular surface receptor 4. Both red blood cells 5 and white blood cells 6 flow in the vessel 1. The white blood cells 6 display endogenous ligands 7 which have chemical and physical characteristics which allow the endogenous ligands 7 to bind to the receptors 4. Once the endogenous ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation.

Figure 2:
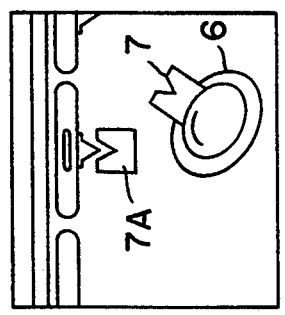
FIG. 2 is a cross-sectional schematic view showing how ligands of the invention might be used as pharmaceuticals to block ELAM-1.

An important aspect of the present invention can be described by referring to FIG. 2. Derivatives of anthraquinone and anthracene are synthesized to act as synthetic ligands shown as 7A. The synthetic ligands 7A adhere to ELAM-1 by themselves and can be formulated into pharmaceutical compositions, which when administered will effectively block the ELAM-1 and prevent the adhesion of an endogenous ligand 7 connected to a white blood cell 6. By administering pharmaceutically effective amounts of synthetic ligands 7A, some, but not all, of the white blood cells will not reach the surrounding tissue 8. By slowing the rate at which the white blood cells reach the surrounding tissue, inflammation can be prevented and/or alleviated.

Figure 3:
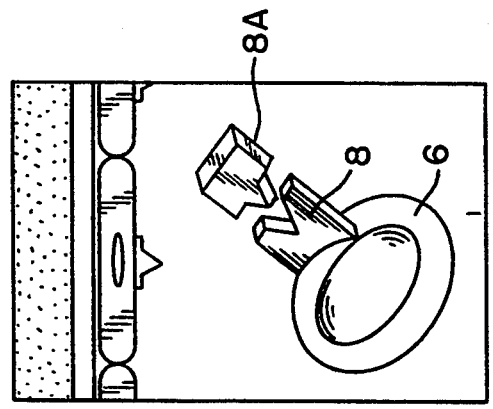
FIG. 3 is a cross-sectional schematic view showing how ligands of the invention might be used as pharmaceuticals to block LECAM-1.

Another important aspect of the invention can be described with reference to FIG. 3. In FIG. 3 the LECAM-1 receptor 8 on the white blood cell 6 is blocked by the synthetic ligand 8A. The present inventors have found that ligands in the form of derivatives of anthraquinone and/or anthracene as per structural formula I can block ELAM-1 and LECAM-1 selectins.

It is known that for an acute inflammatory response to occur, circulating neutrophils must bind to and penetrate the vascular wall and access the site of injury. The derivatives of anthraquinone and anthracene make up the synthetic ligands of the invention. Formulations of such synthetic ligands can prevent an acute inflammation response when administered systemically and/or locally.

A variety of derivatives of anthraquinone and anthracene can be produced as described below. The activity of these derivatives to act as ligands can be tested in an adhesion assay described further below. Such assay can be used to obtain a mixture of molecules which adhere to natural selectins. The invention encompasses derivatives of anthraquinone and/or anthracene which adhere to selectins in this assay to the same or a greater degree as compared with isolated natural ligands. Such derivative/ligands are encompassed by the following general formula:

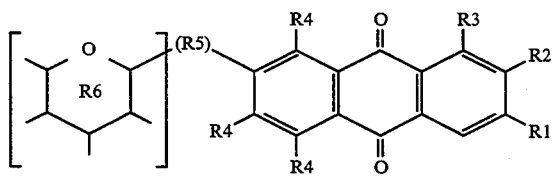

R1 = OH, O-alkyl wherein the alkyl contains 1 to 6 carbon atoms, or O-linker wherein the linker group is an alkyl containing 1 to 12 carbon atoms or a heteroalkyl containing 1 to 12 atoms which contains heteroatoms selected from the group consisting of S, N, and O;

R2 R—COOH, or $CH_2$—O—$CO_2H$, $CH_2O$—R—$CO_2H$, $OCH_2CO_2H$, O—R—O—$SO_3$, O—R—O—$PO_3$ or O—R—$CO_2H$ wherein R is an alkyl containing 1 to 6 carbon atoms;

R3=H, an alkyl containing 1 to 6 carbon atoms or a heteroalkyl containing 1 to 6 atoms with the heteroatom being selected from the group consisting of N, S, and O;

R4=OH, or O—R' wherein R' is an alkyl containing 1 to 6 carbon atoms or a heteroalkyl containing 1 to 6 atoms with the heteroatom being selected from the group consisting of S and N;

R5=—(CH$_2$)$_n$— wherein n is an integer of from 1 to 12 and the —(CH$_2$)$_n$— group may be further attached to a heteroatom selected from the group consisting of N, S and O; and R6=Hexose or a hexNAc, or a disaccharide linked by either α- or β-linkage to R5 through a linking group which includes as a base atom chain comprised of atoms selected from the group consisting of C, O, N and S such that the linking group may be, —O—, or —(CH$_2$)—$_n$ wherein n is an integer of from 1 to 6.

In addition, the invention includes pharmaceutically acceptable salts of compounds of formula I and multivalent derivatives thereof.

Derivatives described above can be synthesized using carminic acid or known anthraquinone derivatives. Carminic acid is the major component of cochineal, a red colored material derived from the insect *Dactylopius cocus* Costa. Cochineal is commercially available and is now widely used as a coloring agent in food, cosmetics and pharmaceutical products. As a therapeutic agent, carminic acid has been found to exhibit antiviral and antitumor activities (see published PCT application WO 91/15200 published Oct. 17, 1991 and Jamison et al. (1988) *Life Sciences* 42, 1477–1488). The present invention relates to the inhibition of the binding of E-, L- and P-selectins to endogenous ligand and molecules such as sialyl-Lewis$^x$ (SLe$^x$) epitopes by administering formulations containing certain derivatives of carminic acid.

Figure 5:
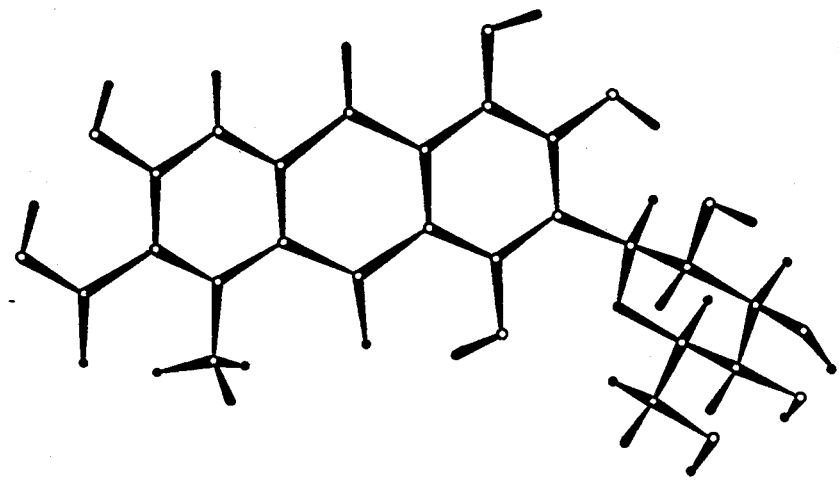
FIG. 5 is a schematic 3-dimensional representation of carminic acid.
Figure 4:
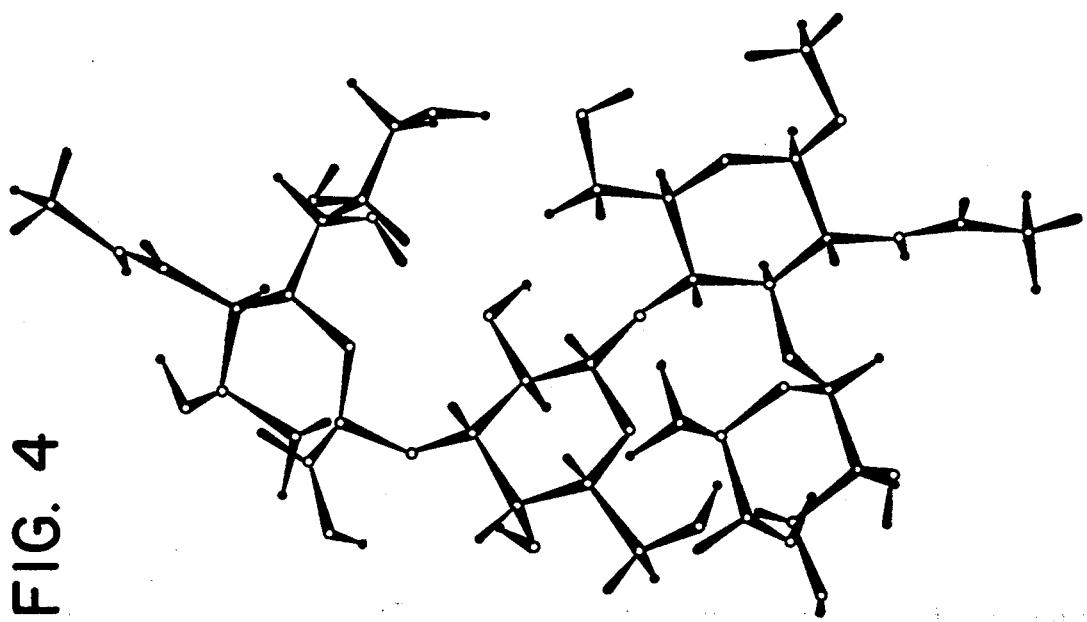
FIG. 4 is a schematic 3-dimensional representation of the ligand known as SLe$^x$.

Carminic acid has structural similarity to a SLe$^x$ pharmacophore model, which can be derived from conformational studies using 500 MHz NMR and computational studies of SLe$^x$-Lac-OSE hexasaccharide. (See FIGS. 4 and 5) Using the pharmacophore model as the structural template, a computer search of the FCD data base can be carried out using MACCS3D software with the following conditions: (i) a compound should have a —COOH moiety; (ii) two or more vicinal hydroxyls; and (iii) a distance of 8–15 Å between COOH and OH groups. The distance constraints may be relaxed in order to either increase or restrict the number of hits in the search. Compounds thus identified may be submitted for biological assay of the type described herein.

The operability of the ligand of the invention can be carried out using a method of assaying candidate ligands for their ability to adhere to selectins such as ELAM-1. The method comprises attaching candidate ligands to a substrate surface and then contacting the substrate surface thereon with recombinant cells, that are genetically engineered to express high levels of ELAM-1, for a sufficient time to allow the cells to adhere to the substrate bearing the candidate ligand. Thereafter, centrifugal force or other appropriate methodology is applied so as to separate away the cells which do not adhere to the substrate. Candidate ligands which adhere to ELAM-1 are determined via the labels on the cells. Such molecules are isolated, characterized, and their structure specifically identified.

B. Assay to Identify Ligand (General)

Radiolabeled COS cells expressing cell surface ELAM-1 may be used as probes to screen derivatives of anthraquinone and/or anthracene. ELAM-1 transfected COS cells adhered to compounds which act as ligands can be resolved on TLC plates or adsorbed on PVC microtiter wells. Adhesion to these compounds my require the presence of other compounds such as calcium.

One mechanism by which glycolipids could mediate intercellular events would involve the recognition of a ligand moiety on one cell (e.g., an endothelial cell) by a specific binding protein (lectin) on an opposing cell (e.g., a leukocyte). Data can be generated using the procedures described herein to show that derivatives of general formula I are capable of participating in the interaction of neutrophils with the surface of cells of activated vascular endothelium. Many protein-protein interactions have been implicated in neutrophil-endothelium transmigration (see Lo, S. K., et al., *J. Immunol.* (1989) 143:3325; Osborn, L., et al., *Cell* (1989) 59:1203; Larsen, F., et al., *Cell* (1989) 59:305; and Arnaout, M. A., *Blood* (1990) 75:1037). While not wishing to be bound to any theory, the present inventors believe it is likely that this lectin-ligand interaction is only one step in a series that result in neutrophil extravasation.

The adhesion of ELAM-1 for compounds of formula I described here may be tested to confirm that these compounds are useful in mediating a specific, but possibly weak adhesion which may be stabilized and elaborated by the participation of other receptors. Compounds with the structural and functional characteristics described herein, or modifications of these structures, are believed to be capable of blocking the interaction of neutrophils with activated vascular endothelium mediated by ELAM-1, and hence provide useful pharmaceutically active agents which can interrupt the adverse effects involved in the interaction of ELAM-1 and circulating neutrophils, e.g., prevent or reduce inflammation.

C. Identification of Putative ELAM-1 Ligands Using Recombinantly Produced Receptor A complete cDNA for the ELAM-1 receptor may be obtained by PCR starting with total RNA isolated from IL-1 stimulated human umbilical vein endothelium. The resulting cDNA may be inserted into the CDM8 plasmid (see Aruffo, A., and Seed, B., *Proc. Natl. Acad. Sci. USA* (1987) 84:8573) and the plasmid amplified in *E. coli.* Plasmid DNA from individual colonies may be isolated and used to transfect COS cells. Positive plasmids may be selected by their ability to generate COS cells that support HL-60 cell adhesion. DNA sequencing can be used to positively identify one of these clones as encoding for ELAM-1 (Bevilacqua, M. P., et al., *Science,* (1989) 243:1160; Polte, T., et al., *Nucleic Acids Res.* (1990) 18:1083; Hession, C., et al., *Proc. Natl. Acad. Sci. USA* (1990)87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT patent application WO90/13300 which was published Nov. 15, 1990, which is incorporated herein by reference).

COS cells, expressing membrane-bound ELAM-1, may be metabolically radiolabeled with $^{32}$PO$_4$ and used as probes in two assay systems to screen for recognition of ligands of formula I. In one method, the compounds may be adsorbed to the bottoms of PVC microtiter wells, while in another they may be resolved on TLC plates. In both assays the compounds may be probed for their ability to support adhesion of ELAM-transfected COS cells, untransfected COS cells, or COS cells transfected with a plasmid containing an irrelevant cDNA, under conditions of controlled detachment force (see Swank-Hill, P., et al., *Anal. Biochem.* (1987) 183:27; and Blackburn, C. C., et al., *J. Biol. Chem.* (1986) 261:2873 each of which is incorporated herein by reference to disclose the details of such assaying methodology).

The "linker" can be used to attach a pharmaceutically effective drug to the ligand. The (Ligand-Linker-Drug) conjugate thus formed provides an effective drug delivery system for the linked drug. It is especially preferred to attach a drug with anti-inflammatory characteristics in that the ligand binds to a selectin receptor which is associated with inflammation. Accordingly, NSAID or non-steroidal anti-inflammatory drugs such as naproxen or ibuprofen which act as anti-inflammatory agents could be administered bound to the ligand and could be administered systemically in smaller mounts than usual while obtaining an equivalent effect or even greater anti-inflammatory effect at the site of inflammation. Other drugs which might be attached include, but are not limited to, antibiotics, vasodilators and analgesics. Such a drug delivery system would reduce any systemic effect normally caused by the drag in that the drugs could be administered in mounts of one-half to one-tenth the normal dose and still obtain the same anti-inflammatory result at the site of inflammation.

D. Determining Putative Ligands

Compounds of formula I can be synthesized, isolated and screened for adhesion of ELAM-transfected COS cells by the PVC microtiter well adsorption assay described in Blackburn et al., J. Biol. Chem. (1986) 261:2873 which is incorporated herein by reference to describe and disclose such a procedure), or by a TLC overlay procedure. Fractions from the Iatrobead column can be pooled based on their ability to support adhesion of ELAM-transfected COS cells in the microtiter assay. Such pools can be run on High Performance Silica TLC (HPTLC) plates in 60:35:10 (chloroform::methanol:0.25% aqueous KCl). Companion plates can be coated with polyisobutyl methacrylate (0.005% in hexane) and probed with ELAM-transfected COS or control COS (metabolically radiolabeled with $^{32}PO_4$) using conditions of controlled detachment force as described in detail in Swank-Hill et al. *Anal. Biochem* (1987) 163:27 which is incorporated herein by reference. Autoradiographs of a TLC plate probed with ELAM-transfected COS cells can be made. The bands of the autoradiographs may be compared with control-COS probed autoradiographs. The pools containing the bands recognized specifically by the ELAM-transfected COS cells can be taken through further purification.

Derivatives at each step of purification can be adsorbed to PVC microtiter wells and probed with ELAM-transfected or control COS cells as described in Blackburn cited above. Results from a given concentration should demonstrate increased specific binding activity with purification.

E. Use and Administration

The compounds of the invention such as various synthetic ligands of structural formula I can be administered to a subject in need thereof to treat the subject by either prophylactically preventing inflammation or relieving it after it has begun. The synthetic ligands are preferably administered with a pharmaceutically acceptable carrier, the nature of the carrier differing with the mode of administration, for example, oral administration, usually using a solid carrier and I.V. administration a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject ligand molecules directly in transdermal formulations with permeation enhancers such as DMSO. Other topical formulations can be administered to treat dermal inflammation.

A sufficient amount of synthetic ligand molecules should be administered to bind to a substantial portion of selectin receptors expected to cause or actually causing inflammation so that inflammation can either be prevented or ameliorated. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

When determining the dose of synthetic ligands to be administered, it must be kept in mind that one may not wish to completely block all of the selectin receptors. In order for a normal healing process to proceed, at least some of the white blood cells or neutrophils must be brought into the tissue in the areas where the wound, infection or disease state is occurring. The amount of the synthetic ligands administered as blocking agents must be adjusted carefully based on the particular needs of the patient while taking into consideration a variety of factors such as the type of disease that is being treated.

It is believed that the synthetic ligands or blocking agents of the present invention can be used to treat a wide range of diseases, including diseases such as rheumatoid arthritis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated cells such as endothelial cells then synthesize the selectin receptors within hours of the cells being damaged. The receptors are extended into the blood vessels where they adhere to ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The ligand molecules of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The ligands in the form of formula I can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985 incorporated herein by reference. The composition or formulation to be administered will, in any event, contain a quantity of the synthetic ligand molecules adequate to achieve the desired state in the subject being treated.

The various synthetic ligand compounds of the present invention can be used by themselves or in combination with pharmaceutically acceptable excipient materials as described above. However, the synthetic ligand compounds of the invention can be made as conjugates wherein the compounds of the invention are linked in some manner to a label. By forming such conjugates, the synthetic ligand compounds of the invention act as biochemical delivery systems for the label so that a site of inflammation can be detected.

The synthetic ligand molecules of the invention could also be used as laboratory probes to test for the presence of ELAM-1 in a sample. Such probes are preferably labeled such as with a radioactive label. There are a number of known labels including radioactive labeled atoms, e.g. radioactive C, O, N, P, or S, fluorescent dyes and enzyme labels which can be attached to the synthetic ligands of the invention using known procedures. Labels as well as methods of attaching labels to sugar moieties are disclosed in U.S. Pat. No. 4,849,513 issued Jul. 18, 1989 to Smith et al. which patent is incorporated herein by reference to disclose labels and methods of attaching labels.

EXAMPLES

The following examples are provided so as to provide those of ordinary skill in the art with a complete disclosure and description of how to synthesize derivatives of the invention and determine their ability to act as ligands are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

For further details regarding the procedures described below, reference may be made to the following publications which are incorporated herein by reference:

1. P. Alleve, M. Auastasia, P. Ciuffreda, A. Fiecchi, A. Scala, S. Binghan, J. Chem. Soc., Chem. Comm. 1319, 1991.
2. P. Allevi, M. Anastasia, P. Ciufreda, A. Fiecchi and A. Scala, J. Chem. Soc., Chem. Comm. 1245, 1987.
3. M. S. Cat and D. X. iu, Carbohydrate Res., 191 (1989), 125–129.
4. P. W. Austin, F. E. Hardy, J. R. Buchanan, J. Braddiley, J. Chem. Soc., Chem. Comm. 2128 (1964).

EXAMPLE 1

Ethyl [(1-methyl-3,5,8,9,10-pentamethoxyl-7-β-L-(2,3,4-O-tribenzylfucopyranosyl)]-2-anthranene Carboxylate 1

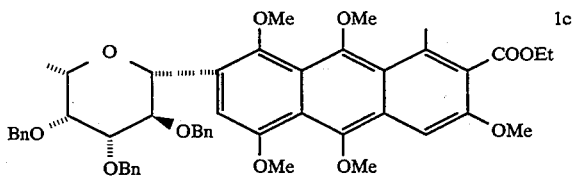

To a solution of 1.5 g (3.62 mmole) of ethyl 1-methyl-3,5,8,9,10-pentamethoxyl-2-anthracene carboxylate 1a (Ref. 1 and 2) in 30 ml of dry acetonitrile (stored over 4 angstrom molecular sieves) at −20° C. was added with a solution of 2.4 ml of boron trifloride etherate. To this was cannulated with a solution of 2.92 g (5.5 mmole) of 2,3,4-O-tribenzyl-1-(2-trifluoroacetoxy)-β-L-fucopyranose 1b (Ref. 3 and 4) over 5 min. This reaction mixture was then stirred at −20° C. for 1 hr., r.t. for 14 hrs and poured into a cold solution of 50 ml saturated sodium bicarbonate solution. Acetonitrile was then removed in rotavap and the resulting mixture extracted with 3×75 ml of ethyl acetate. The combined organic extracts were washed with 30 ml of brine, dried over sodium sulfate, filtered and concentrated. The residue was then purified on a silica gel column (200 g silica gel, hexane and ethyl acetate from 2 to 1 to 1 to 1) to provide 1.12 g (1.35 mmole, 37.3%) of the carboxylate 1c as a white solid.

7-β-L-Fucopyranosyl-1-methyl-3,5,8,9,10-pentamethoxyl-2-anthranene Carboxylic Acid 1

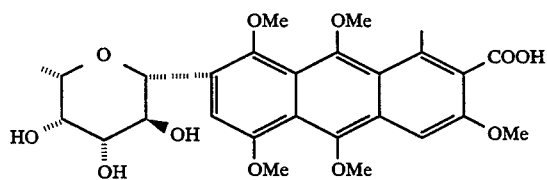

A solution of 300 mg (0.36 mmole) of carboxylate 1c in 2 ml each of methanol and acetic acid was stirred with 100 mg of 10% palladium on carbon under 1 atm. of hydrogen gas for 24 hrs. The mixture was diluted with 10 ml of methanol, filtered through a bed of celite which was washed with 3×10 ml of methanol and the combined filtrate concentrated in vacco to provide the crude triol. Without purification, this material was refluxed with 5 ml of methanol and 2 ml of 2N sodium hydroxide for 3 hrs. Upon acidification, mixture was extracted with 3×30 ml of chloroform. The combined organic extracts were washed with 50 ml of brine solution, dried over sodium sulfate, filtered and concentrated. Crystallization of the crude acid with methanol and diisopropyl ether gave 150 mg (0.28 mmole, 78%) the acid 1.

EXAMPLE 2

7-β-L-Fucopyranosyl-1-methyl-3,5,6-trimethoxyl-9,10-anthraquinone-2-carboxylic Acid 2

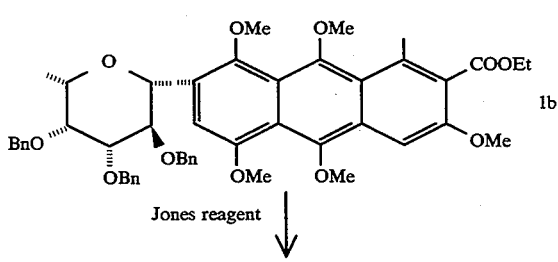

Jones reagent ↓

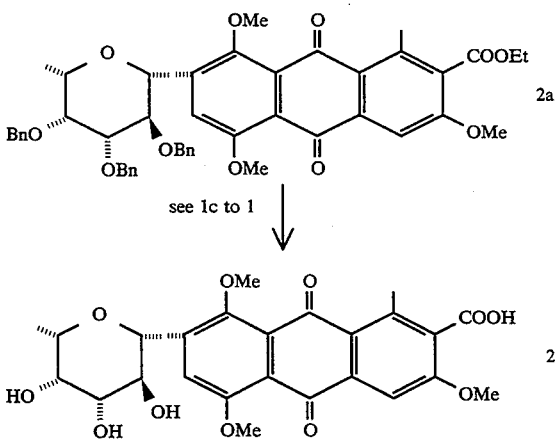

see 1c to 1 ↓

Ethyl 7-β-L-fucopyranosyl-1-methyl-3,5,6-trimethoxyl-9,10-anthraquinone-2-carboxylate 2a

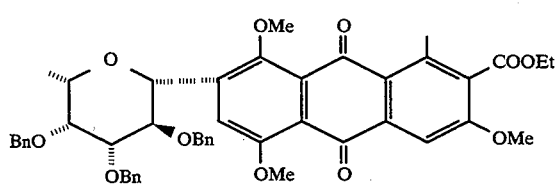

A solution of 305 mg (0.67 mmole) of 1c of 5 ml of acetone at 0° C. was added 2 ml of Jones reagent. The solution was stirred at 0° C. for 1 hr, poured into 20 ml of water and extracted with 2×50 ml of dichloromethane. Combined organic extracts were washed with 20 ml of brine, dried over sodium sulfate, filtered and concentrated. The crude anthraquinone 2a (250 mg) was used as such for the following deprotection steps.

7-β-L-Fucopyranosyl-1-methyl-3,5,6-trimethoxyl-9,10-anthraquinone-2-carboxylic Acid 2

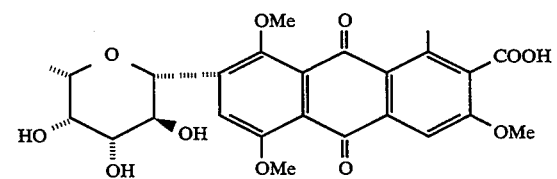

Under the identical reaction conditions for 1c to 1, the debenzylation and hydrogenation of 2a gave 120 mg (0.24 mmole, 37% from 1c) upon crystallization in methanol and diisopropyl ether.

EXAMPLE 3

7-β-L-Fucopyranosyl-1-methyl-3,5,6-trihydroxy-9,10-anthraquinone-2-carboxylic Acid 3

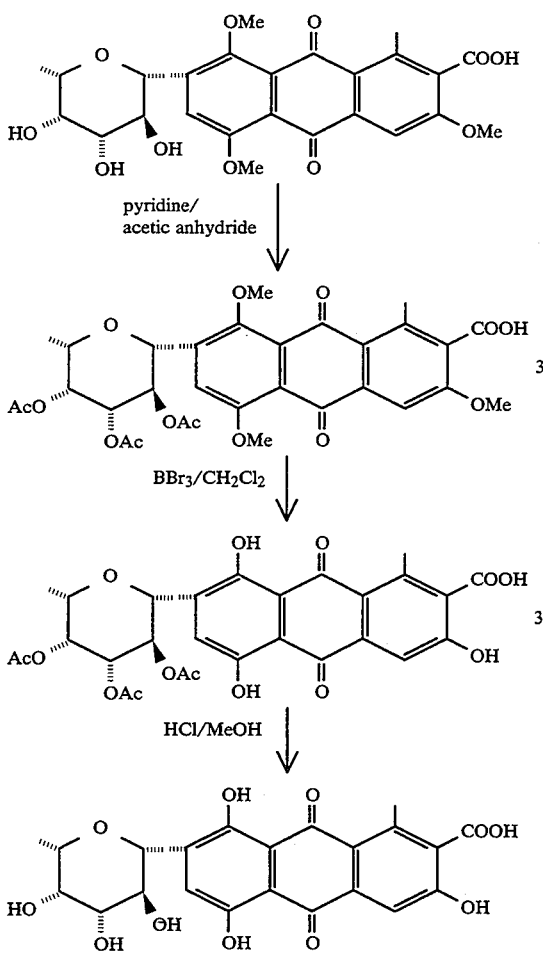

1-methyl-7-β-L-(2,3,4-O-triacetylfucopyranosyl)-3,5,8-trimethoxyl-9,10-anthraquinone-2-carboxylic Acid 3a A sample of 420 mg (0.84 mmole) of acid 2 was stirred with 3 ml each of pyridine and acetic anhydride for 14 hrs. All volatile material was removed in vacco. Residue was dissolved in 50 ml of dichloromethane. This was then washed with ml of 1N HCl solution, 20 ml of brine, dried over sodium sulfate, filtered and concentrated. The residue was dissolved in 2 ml of dichloromethane and precipitated with diisopropyl ether. Suction filtration provided 365 mg (0.68 mmole, 81.1%) of acetate 3a as a yellow solid.

7-β-L-Fucopyranosyl-1-methyl-3,5,6-trihydroxy-9,10-anthraquinone-2-carboxylic Acid 3

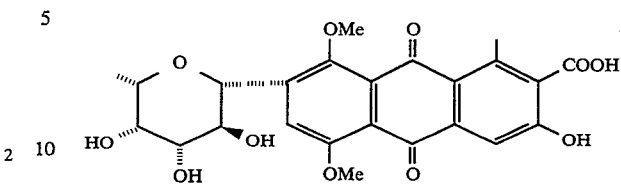

A solution of 250 mg (0.47 mmole) of acid 3a in 5 ml of dichloromethane at −40° C. was added with 0.5 ml of boron tribromide. The reaction mixture was stirred at −40° C. for 3 hrs, −10° C. for 3 hrs and poured into 20 ml of chilled water. This was then extracted with 3×50 ml of dichloromethane. The combined organic extracts were then washed with 20 ml of brine, dried over sodium sulfate, filtered and concentrated to give the crude anthraquinone 3b as an orange solid. This solid was then refluxed in 10 ml of methanol with 2 ml of 1N HCl for 5 hrs. All the volatiles were removed in vacco and upon crystallization with methanol 120 mg (0.26 mmole, 55.5%) of acid 3 was obtained.

EXAMPLE 4

For further details regarding the procedures described below, reference may be made to the following publications which are incorporated herein by reference:

1. O. Dimroth and H. Kammerer, *Chem. Ber.*, 1920, 563B, 471.
2. J. F. W. McOmie and J. M. Blatchly, *Organic Reactions*, 1960, 19, 199.

7-β-L-Fucopyranosyl-1-methyl-3,5,6,8-tetrahydroxy-9,10-anthraquinone-2-carboxylic Acid 4

A mixture of 236 mg (0.42 mmole) of 3b and 2.12 g of lead tetraacetate in 2 ml of acetic acid was stirred at 55° C. for 6 hrs. The cooled reaction mixture was poured into 100 ml of dichloromethane and filtered through a bed of celite which was washed with 50 ml of dichloromethane. The combined filtrates were then washed with 50 ml of water, 30 ml of saturated sodium bicarbonate solution, 30 ml of brine, dried over sodium sulfate and filtered through celite. After all the volatiles were removed, the crude orange solid was refluxed in 5 ml of methanol and 3 ml of 1N HCl solution for 5 hours. All the volatiles were then removed and upon crystallization of the crude product in methanol yielded 65 mg (0.14 mmole, 32% yield) of acid 4 as an orange solid.

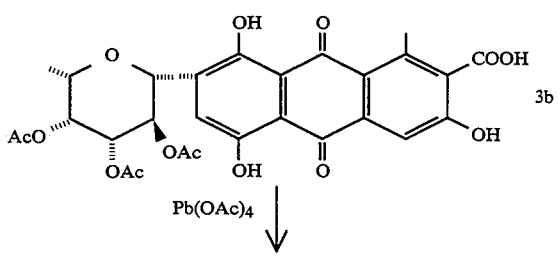

-continued

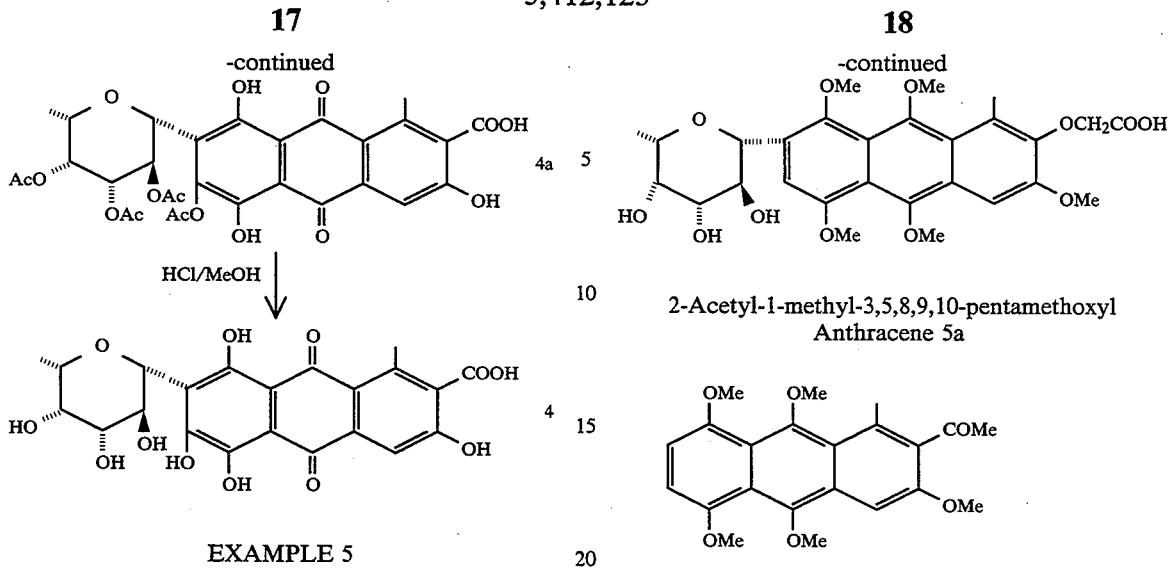

EXAMPLE 5

2-[7-β-L-Fucopyranosyl-1-3,5,8,9,10-pentamethoxyl-2-anthracenoxy] Acetic Acid 5

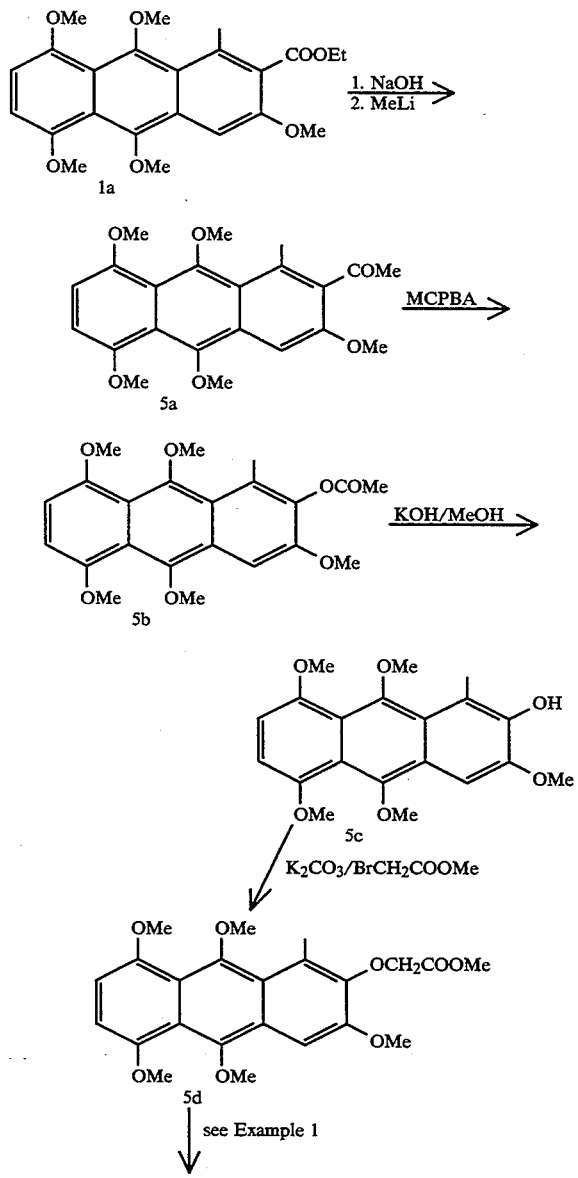

see Example 1

2-Acetyl-1-methyl-3,5,8,9,10-pentamethoxyl Anthracene 5a

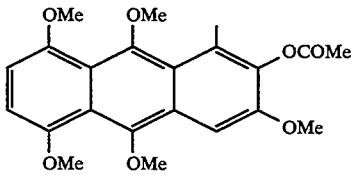

A sample of 925 mg (2.23 mmole) of 1a was stirred with 5 ml of methanol and 3 ml of 2N sodium hydroxide at r.t. for 2 hrs. This was then extracted with 1N HCl and extracted with 3×50 ml of chloroform. The combined organic extracts were washed with 30 ml of brine, dried over sodium sulfate, filtered and concentrated to give 830 mg (2.16 mmole) of the crude acid. This solid was then stirred in 10 ml of ether at −78° C. and added with 4.0 ml (5.6 mmole) of 1.4M methyllithium solution in ether. Upon stirring at −78° C. for 30 minutes, the cooling bath was removed and mixture stirred at r.t. for 14 hours. This mixture was then poured into 10 ml of 0.1N HCl and extracted with 3×80 ml of ether. The combined organic extracts were washed 15 ml of saturated sodium bicarbonate solution, 30 ml of brine, dried over sodium sulfate, filtered and concentrated. The crude ketone was then purified on a silica gel column (150 g, hexane and ethyl acetate from 10 to 1 to 4 to 1) to provide mg (1.17 mmole, 52.4%) of the ketone 5a as a foamy solid.

1-Methyl-3,5,8,9,10-pentamethoxyl-2-anthracenol 5b

A solution of 1.2 g (3.2 mmole) of ketone 5a, 2.1 g of 3-chloroperoxybenzoic acid and 200 mg of sodium bicarbonate in 15' ml of chloroform was refluxed for 30 hours. The cooled mixture was then filtered and washed with 30 ml of chloroform. The combined filtrates were then concentrated and dissolved in 100 ml of ethyl acetate. This was then washed with 20 ml of 1N sodium hydroxide, 30 ml of brine, dried over sodium sulfate, filtered and concentrated. The crude residue was dissolved in 10 ml of methanol and added 5 ml of 1N potassium hydroxide solution. The solution was stirred at r.t. for 2 hrs and acidified with 1N HCl. This was then extracted with 3×100 ml of ethyl acetate. The combined organic extracts were washed with 20 ml of saturated sodium bicarbonate solution, 20 ml of brine, dried over sodium sulfate, filtered and concentrated. The crude was then purified on a silica gel column (150 g, hexane and ethyl acetate, 6 to 1) to provide 605 mg (1.82 mmole 56.9%) of the anthracenol 5b.

Methyl 2-(1-methyl-3,5,8,9,10-pentamethoxyl-2-anthracenoxy) Acetate 5c

Following the similar procedure sequence of 1a to 1 (glycoside formation, debenzylation and saponification), acetic acid derivative 5 was obtained.

EXAMPLE 6

3-(7-β-1-fucopyranosyl-1-methyl-3,5,8,9,10-pentamethoxyl-2-anthracenyl)-n-propionic Acid 6

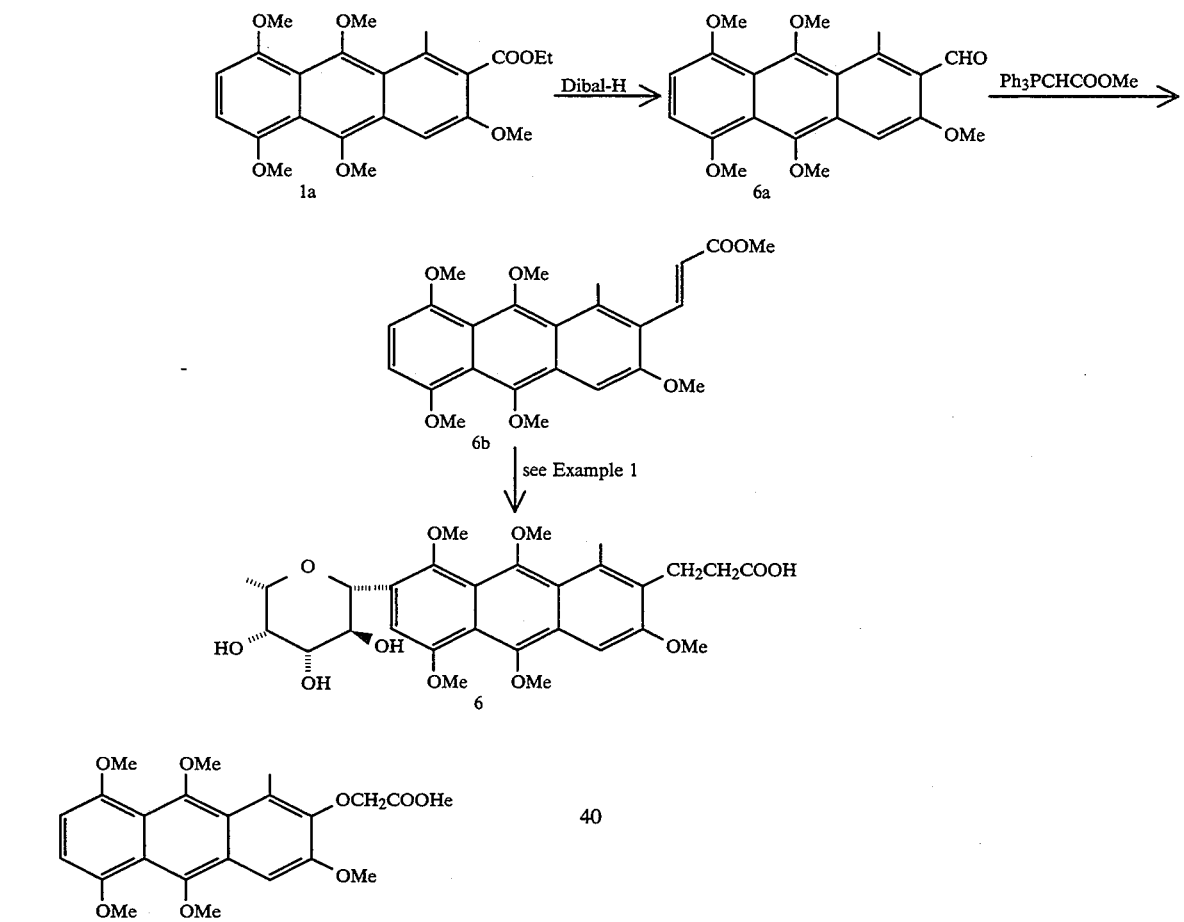

A solution of 600 mg( 1.68 mmole) an anthracenol 5b in 5 ml of dry dimethylforamide was stirred with 463 mg (3.3 mmole) of finely powdered potassium carbonate for 30 minutes. This was then added with 312 μl (3.3 mmole) of methyl bromoacetate. This reaction mixture was then stirred at r.t. for about 48 hours, poured into 30 ml of water and extracted with 3×80 ml of ethyl acetate. The combined organic extracts were then washed with 30 ml of brine, dried over sodium sulfate, filtered and concentrated. The crude ester was then purified on a silica gel column (150 g, hexane and ethyl acetate, 6 to 1) to provide 664 mg (1.55 mmole, of the ester 5c.

2-[7-β-L-Fucopyranosyl-1-methyl-3,5,8,9,10-pentamethoxyl-2-anthracenoxy] Acetic Acid 5

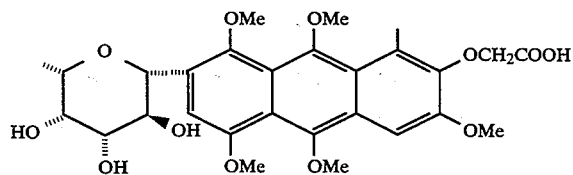

1-Methyl-3,5,8,9,10-pentamethoxy-2-anthraldehyde 6a

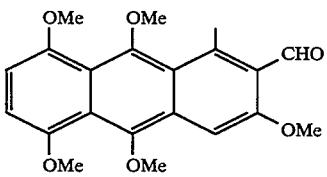

A solution of 1.2 g (2.9 mmole) of ester 1a in 20 ml of dichloromethane 15°–78° C. was added with 2.2 ml (3.19 mmole) of 1.5M diisobutylalumium hydride in toluene. This solution was stirred at −78° C. for 1 hr., −40° C. for 1 hr and quenched with 1 ml of methanol. This mixture was then diluted with 200 ml of ether and added with 2 ml of brine solution. Upon stirring at r.t. for 20 minutes, this was added with two tablespoons of magnesium sulfate, stirred at r.t. for 20 minutes and filtered through celite. The celite cake was washed with another 100 ml of ether and the combined filtrates were concentrated. The crude was then purified on a silica gel column (150 g, hexane and ethyl acetate, 6 to 1) to provide 900 mg (2.77 mmole, 95.6%) of aldehyde 6a.

(E)
Ethyl-3-(1-methyl-3,5,8,9,10-pentamethoxyl-2-anthracenyl)-propenate 6b

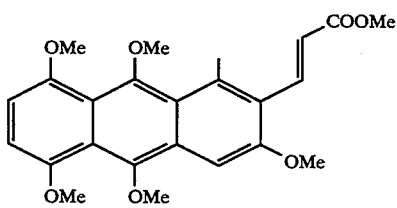

A solution of 790 mg (2.27 mmole) of (carbethoxymethylene)triphenylphosphorane and 524 mg (1.51 mmole) of aldehyde 6a in 10 ml of tetrahydrofuran was refluxed for 6 hrs. The cooled mixture was evaporated and the crude purified on a silica gel column (150 g, hexane and ethyl acetate, 5 to 1) to provide 749 mg (1.7 mmole, 75%) of ester 6b.

3-(7-β-L-Fucopyranosyl-1-methyl-3,5,8,9,10-pentamethoxyl-2-anthracenyl)-n-propionic Acid 6

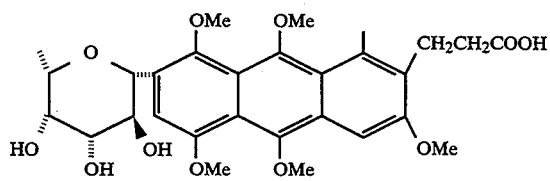

C-Glycoside formation, debenzylation including hydrogenation on the double bond and saponification of 6b (see Example 1 for similar conversion) provided 6.

EXAMPLE 7

[(7-β-L-Fucopyranosyl-1-methyl-3,5,8,9,10-pentamethoxyl-2-anthracenylmethoxy] Acetic Acid 7

2-Hydroxymethyl-1-methyl-3,5,8,9,10-pentamethoxyl Anthracene 7a

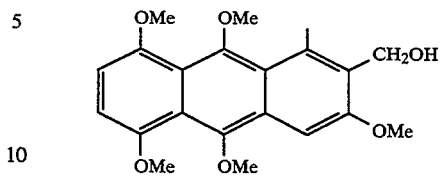

To a solution of 1.2 g (3.12 mmole) of the crude acid 7 (see Example 5) in 10 ml of tetrahydrofuran at 0° C. was added a solution of 2.5 ml of 2M borane dimethylsulfide in tetrahydrofuran. The reaction mixture was stirred at 0° C. for 1 hr., carefully quenched with 1 ml of water and poured into 20 ml of 0.1N sodium hydroxide. This was then extracted with 3×70 ml of ethyl acetate. The combined organic extracts were then washed with 50 ml of brine, dried over sodium sulfate, filtered and concentrated. The crude was then purified on a silica gel column (150 g, hexane and ethyl acetate, 2 to 1) to provide 1.0 g (2.87 mmole, 92%) of alcohol 7a.

Methyl [(1-methyl-3,5,8,9,10-pentamethoxyl-2-anthracenyl) methoxyl] Acetate 7b

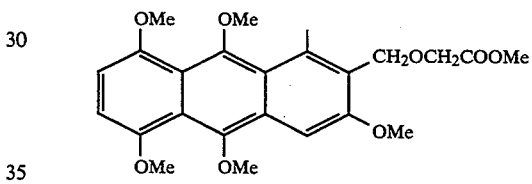

To a solution of 950 mg (2.14 mmole) of alcohol 7a in 12 ml of tetrahydrofuran at 0° C. was added 128 mg of sodium hydride (60% dispersion, 3.21 mmole) in one portion. The mixture was then stirred at 0° C. for 30

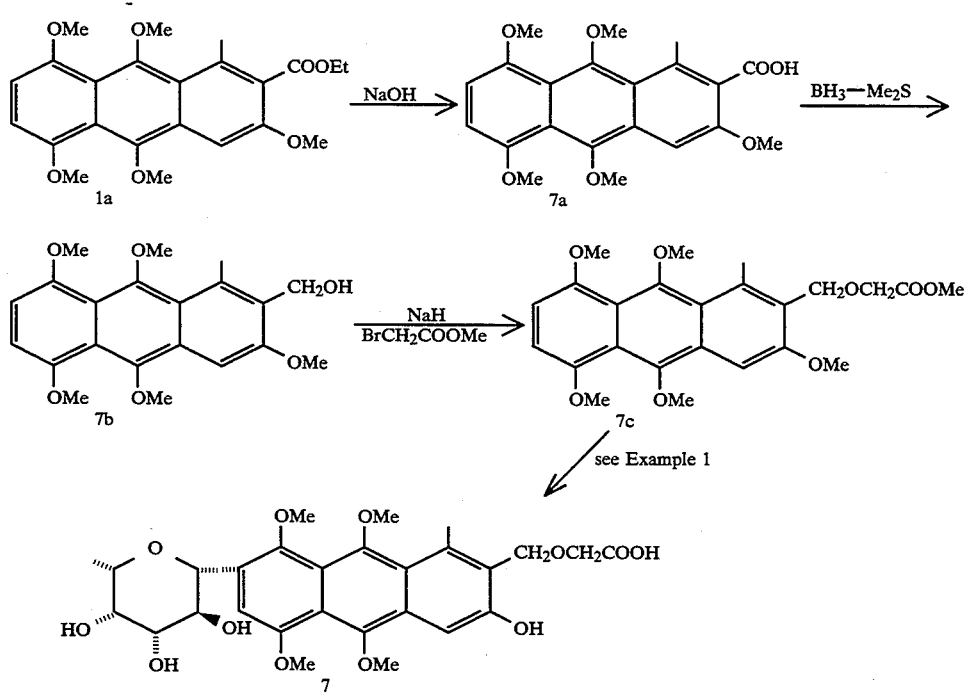

minutes and added with 818 μl (8.56 mmole) of methyl bromoacetate. The reaction mixture was then stirred at r.t. for 40 hrs., poured into 20 ml of water and extracted with 3×70 ml of ethyl acetate. The combined organic extracts were washed with 30 ml of brine, dried over sodium sulfate, filtered and concentrated.

The crude material was then purified on a silica gel column (150 g, hexane and ethyl acetate, 4 to 1) to furnish 629 mg (1.42 mmole, 66.4%) of ester 7b.

(7-β-L-Fucopyranosyl-1-methyl-3,5,8,9,10-pentamethoxyl-2-anthracenyl)methoxy] Acetic Acid 7

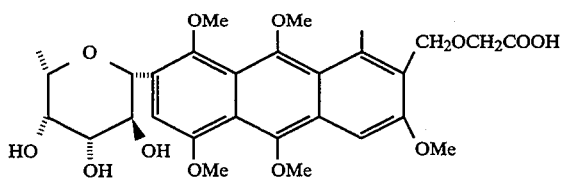

C-Glycoside formation, debenzylation on the double bond and saponification of 7b (see example 1 for similar conversion) provided 7.

EXAMPLE 8

1,6-Bis-(7-β-L-fucopyranosyl-1-methyl-5,8,9,10-tetramethoxyl-3-anthrancenosyl)-n-hexane 8

Ethyl (3-hydroxy-1-methyl-5,8,9,10-tetramethoxyl-2-anthracene) Carboxylate 8a

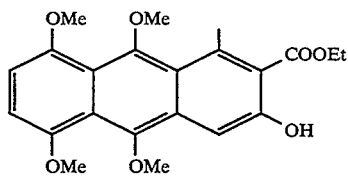

References
H. Nagoioka, G. Schmid, H. Iio and Y. Kishi, *Tetra. Lett.*, 22, 899 (81)

To a solution of 924 mg (2.2 mmole) of 1a in 15 ml of dichloromethane at −30° C. was added 2.5 ml of 1.0M boron trichloride solution in dichloromethane. This solution was stirred at −30° C. for 12 hrs., poured into 30 ml of cold saturated sodium bicarbonate solution and extracted with 3×75 ml of ethyl acetate. The combined organic extracts were washed with 30 ml of brine, dried over sodium sulfate, filtered and concentrated. The crude was then purified on a silica gel column (150 g, hexane and ethyl acetate, 4 to 1) to furnish 460 mg of anthracenol 8a.

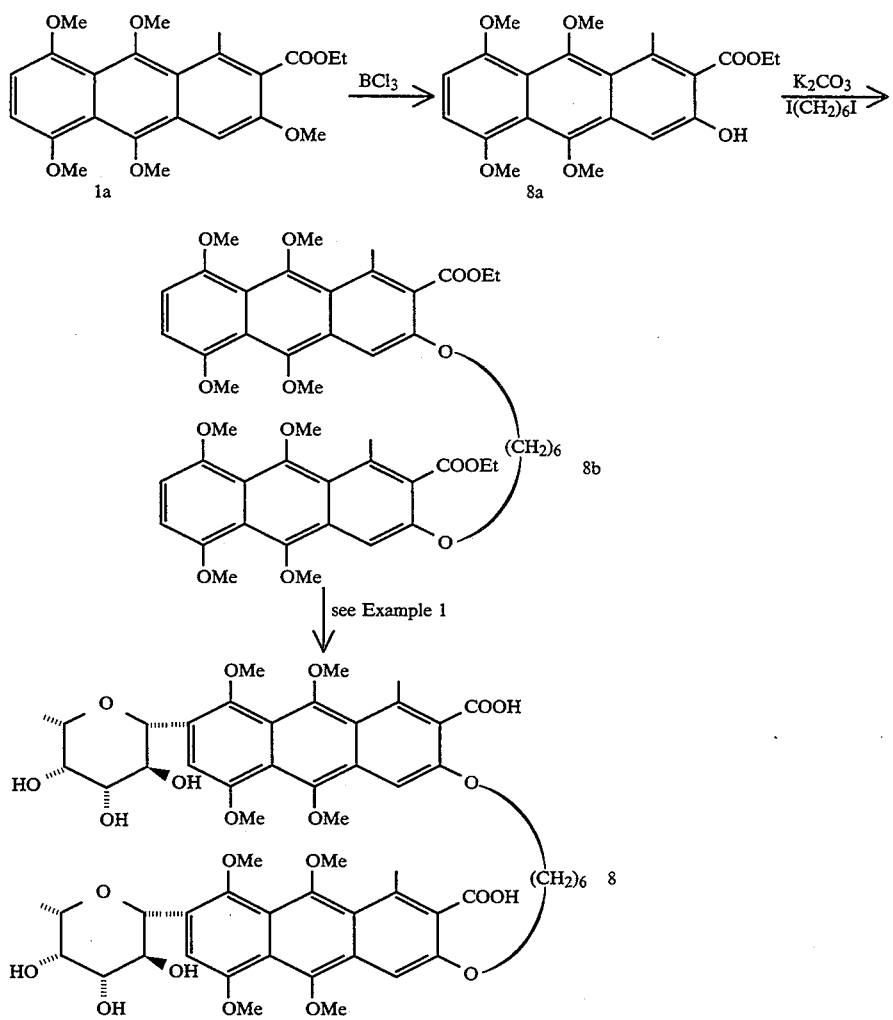

1,6 Bis(2-carethoxyl-1-methyl-5,8,9,10-tetramethoxyl-3-anthracenoxy)-n-hexane 8b

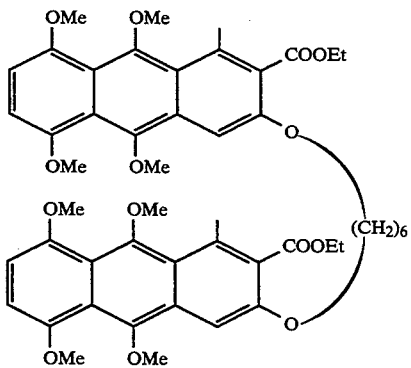

To a solution of 400 mg (1.0 mmole) of anthracenol 8a in 4 ml of dimethylforamide was stirred with 400 mg of finely powdered potassium carbonate. This was then added with 85 μl of diiodohexane. This reaction mixture was then heated at 45° C. for 2 hrs and poured into 20 ml of water. This was then extracted with 3×50 ml of ethyl acetate. The combined organic extracts were then washed with 20 ml of 5% sodium bisulfite solution, 30 ml of brine, dried Over sodium sulfate, filtered and concentrated. The divalent compound 8b (230 rag, 0.28 mmole, 28%) was obtained after purification on a silica gel column (200 g, twice, hexane and ethyl acetate, 4 to 1).

1,6-Bis(7-β-L-fucopyranosyl-1-methyl-5,8,9,10-tetramethoxyl-3-anthrancenoxyl)-n-hexane 8

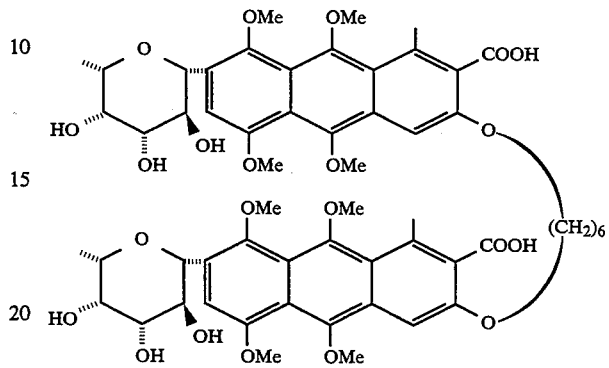

Transformation of 8b to 8 followed the exact procedure as described for Example 1. The overall yield was 15%.

EXAMPLE 9

7-[2-(1-β-L-Fucopyranosyl)-ethyl]-1-methyl-3,5,8,9,10-pentamethoxyl-2-anthracene Carboxylic Acid 9

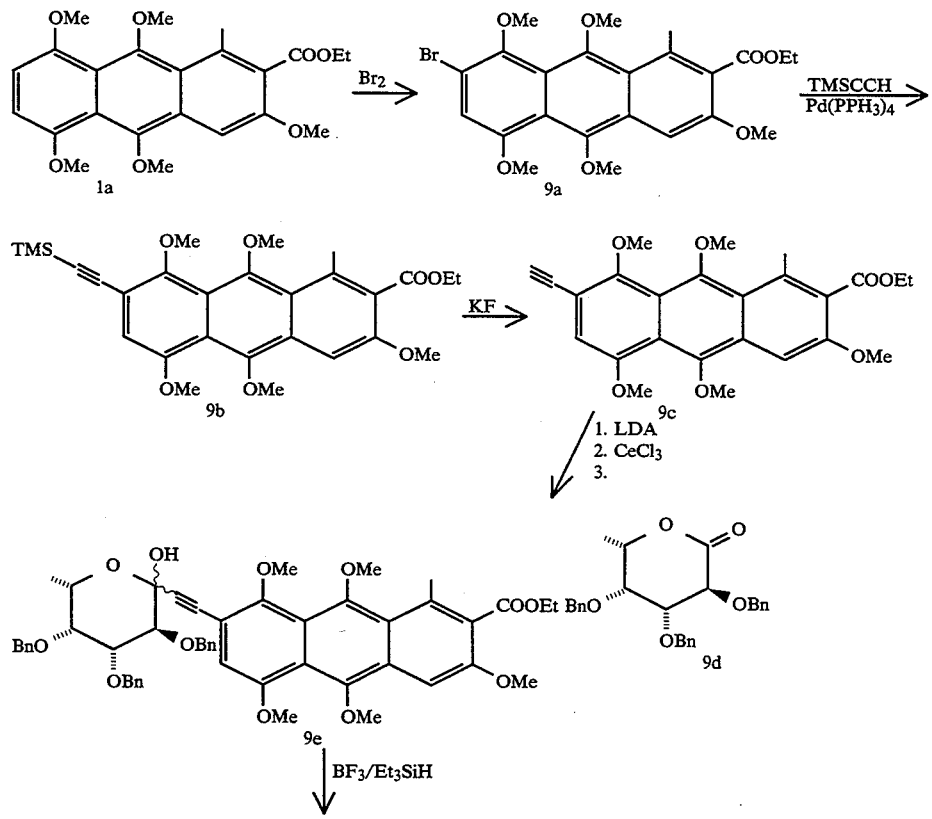

-continued

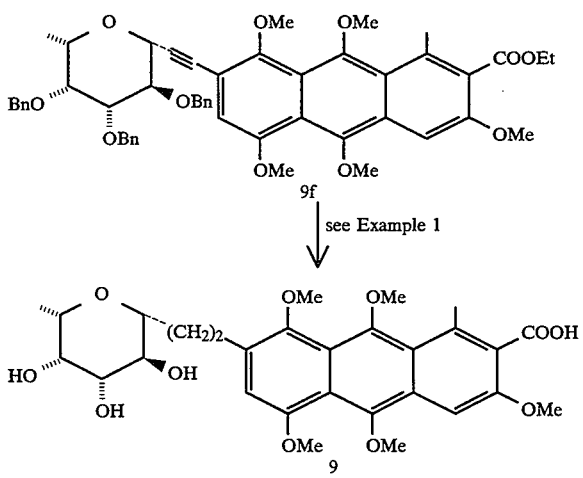

9f see Example 1

↓

9

Ethyl (7-Bromo-1-methyl-3,5,8,9,10-pentamethoxyl-2-anthracene) Carboxylate 9a

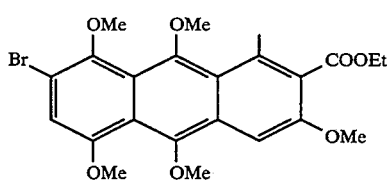

To a solution of 1.2 g (2.9 mmole) of ester 1a in 3 ml of dichloromethane was added dropwise a solution of 3.2 ml of 1M bromine in carbon tetrachloride. After addition, the mixture was stirred at r.t. for 1 hr. and worked up with 20 ml of 5% sodium bisulfite and 3×50 ml of ethyl acetate. The crude was then purified on a silica gel column (200 g, hexane and ethyl acetate, 6 to 1) to give 960 mg (1.95 mmole, 67%) of the bromide 9a.

Ethyl 1-Methyl-3,5,8,9,10-pentamethoxyl-7-(1-trimethylsilyl ethynl)-2-anthracenyl Carboxylate 9b

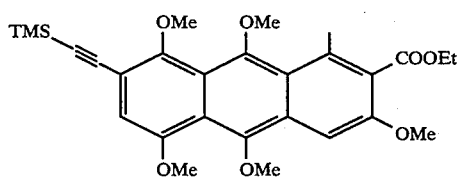

References
1. S. Takahashi, Y. Kuroyama, K. Somogashira and N. Hagihara, *Synthesis*, 627 (1980).
2. Ames, D. E., Bull, D. *Synthesis*, 364 (1981).

A solution containing 900 mg (1.83 mmole) of bromide 9a, 530 μl of triethylamine, 35 mg of copper (1) iodide and 214 mg of tetrakis-(triphenylphosphine) palladium(0) in 50 ml of dimethylforamide was heated at 85° C. for 6 hrs. The mixture was then poured into 30 ml of water and extracted with 3×50 ml of ethyl acetate. The combined organic extracts were then washed with 30 ml of brine, dried over sodium sulfate, filtered and concentrated. The crude product was subjected to desilylation directly as shown next.

Ethyl 7-Ethynl-1-methyl-3,5,8,9,10-pentamethoxyl-2-anthracene Carboxylate 9c

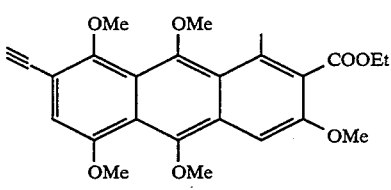

The crude 9b (from 900 mg bromide 9a) in 10 ml of a solvent mixture of acetonitrile and water (9 to 1) was stirred with 500 mg of potassium fluoride dihydrate overnight. The mixture was then poured into 30 ml of water and extracted with 3×70 ml of ethyl acetate. The combined organic extracts were then washed with 30 ml of brine, dried over sodium sulfate, filtered and concentrated. The crude was then purified on a silica gel column (150 g, hexane and ethyl acetate, 5 to 1) to provide 621 mg (1.42 mmole, 78% from 9a) acetylene 9c.

Ethyl 1-Methyl-3,5,8,9,10-pentamethoxyl-7-[2-(b-L-2,3,4-O-tribenzylfucopyranosyl)ethyl-2-anthracene Carboxylate 9d

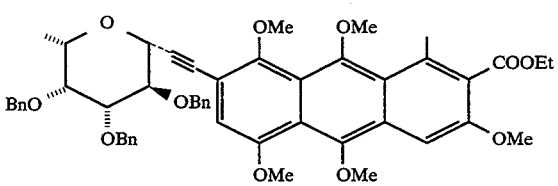

Reference
S. Czernecki and G. Ville, *J. Org. Chem.*, 54, 610 (1989)
To a solution of 400 ml (2.86 mmole) of dry diisopropylamine in 6 ml of tetrahydrofuran at 0° C. was added a solution of 1.6 ml of 1.6M n-butyllithium in hexanes. The solution was stirred at 0° C. for 15 minutes, cooled at -78° C. and cannulated with a solution of 1.32 g (2.6 mmole) of acetylene 9b in 5 ml of tetrahydrofuran over 3 minutes. The mixture was then stirred at −78° C. for 30 minutes, −40° C. for 30 minutes and added with 969 mg (2.6 mmole) of cerium chloride (dried in vacco at 50° C. for 24 hrs before use) in one portion. After stirring at −40° C. for 30 minutes, a solution of 862 mg (2.0 mmole) of lactone 9d in 3 ml of tetrahydrofuran was cannulated into the above mixture. The mixture was then stirred at −40° C. for 1 hr., gradually warmed up to r.t. by removing the cooling bath and stirred for 12 hrs. The mixture was then poured into 30 ml of water and extracted with 3×100 ml of ethyl acetate. The combined organic extracts were washed with 50 ml of brine, dried over sodium sulfate, filtered and concentrated. The crude lactol was then immediately stirred with 0.5 ml of triethylsilane and 0.2 ml of boron trifloride in 3 ml of acetonitrile at −40° C. for 4 hrs. The mixture was then poured into 30 ml of cold water and extracted with 3×50 ml of ethyl acetate. The combined organic extracts were washed with 20 ml of saturated sodium bicarbonate solution, 20 ml of brine, dried over sodium sulfate, filtered and concentrated. The crude product was then purified on a silica gel column (150 g, hexane and ethyl acetate, 3 to 1) to provide 512 mg (0.6 mmole, 30%) of ester 9c.

7-[2-(1-β-L-Fucopyranosyl)-ethyl]-1-methyl-3,5,8,9,10-pentamethoxyl-2-anthracene Carboxylic Acid 9

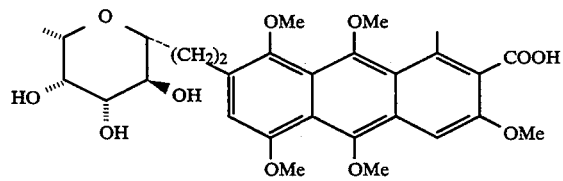

Hydrogenation followed by saponification (see Example 1 ) on 9c provided acid 9.

EXAMPLE 10

7-β-L-Fucopyranosyl-1-methyl-3,8,9,10-tetramethoxyl-2-anthracene Carboxylic Acid 10

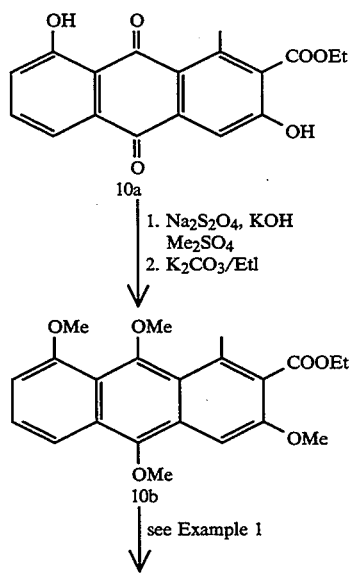

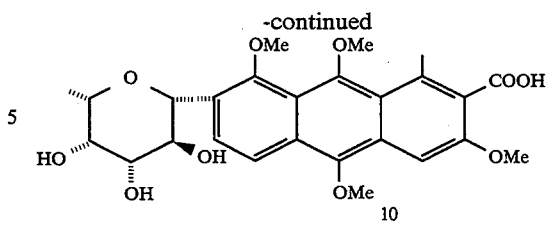

Ethyl 1-methyl-3,8,9,10-tetramethoxyl-2-anthracene Carboxylate 10b

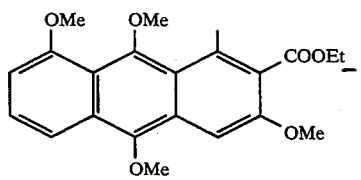

References
1. D. W. Cameron, D. J. Deutscher, G. I. Feutrill and P. G. Griffiths, *Aust. J. Chem.*, 34, 2401 (1981).
2. G. A. Kraus and T. O. Man, *Synthetic Communication*, 16(9), 1037 (1986).

To a solution of 350 mg (1.52 mmole) of ethyl 3,8-dihydroxy-1-methyl-9,10-anthraquinone-2-carboxylate and 75 mg of tetrabutylammonium bromide in 10 ml of tetrahydrofuran and 4 ml of water was added with 10 mmole of aqueous sodium dithionite. After 25 minutes, 9 ml of 4N aqueous potassium hydroxide was added. After 25 minutes, 4 ml of dimethylsulfate was added and the combined mixture stirred at r.t. for 14 hrs. The crude product was then acidified with 6N of HCl and extracted with 3×50 ml of ethyl acetate. The organic extracts were then washed with 30 ml of brine, dried over sodium sulfate, filtered and concentrated. The crude acid was then stirred with 200 mg of pulverized potassium carbonate and 0.3 ml of iodoethane in 5 ml of tetrahydrofuran for 12 hrs. This was then worked up with 20 ml of water and 100 ml of ethyl acetate. The crude ester was then purified on a silica gel column (150 g, hexane and ethyl acetate, 5 to 1) to provide 437 mg (1.14 mmole, 75%) of the ester 10b.

7-β-L-Fucopyranosyl-1-methyl-3,8,9,10-tetramethoxyl-2-anthracene Carboxylic Acid 10

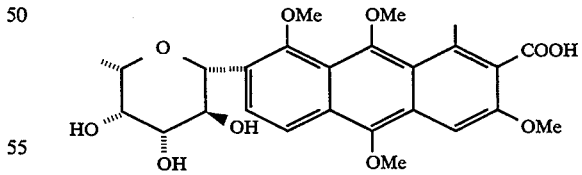

Manipulation of 10a to 10 followed the exact protocol as described in Example 1.

EXAMPLE 11

Inhibition of Selectin Binding to SLe$^x$ by Multivalent Anthraquinone Derivative, Sennoside B The capacity of the multivalent anthraquinone derivative, Sennoside B, to inhibit selectin binding to sLex was tested essentially as described by Foxall, C., et al J. Cell Biol., vol. 117, pages 895–902 (1992) using selectin IgG chimeras.

The following assay procedure was used. sLex at 25 pm/well was evaporated onto microtiter wells in MeOH and H2O overnight. The plates were washed with H2O and blocked with 5% BSA in PBS with 1 mM Ca for 1 hour. L-selectin was diluted to 35 ng/ml in 1% BSA PBS with 1 mM Ca and 1:1500 biotinylated goat F(ab') anti-human IgG Fc (CalTag, corp.) and streptavidin-alkaline phosphatase. E-selectin at 50 ng/ml and P-selectin at 750 ng/ml were similarly diluted with 1:1000 dilutions of biotinylated goat F(ab') anti-human IgG Fc and streptavidin-alkaline phosphatase. These were allowed to complex for 15 minutes at 37° C.

Part of each selectin solution was made 2 mM with sennoside B (obtained from Pfaltz and Bauer, Inc., Waterbury, Conn.) The most concentrated solutions were diluted with the selectin solution to yield 3 solutions each ½ as concentrated as the previous. The solutions with selectin and inhibitor were incubated for 45 minutes at 37° C.

Blocking solution was washed off the plates with PBS; solutions (50 ul/well) were added to the plate and incubated for 45 minutes at 37° C. The plates were then washed 3 times with PBS and H2O. 50 ul/well of I mg/ml of p-nitrophenylphosphate in 1M diethanolamine with 0.001% MgCl2, pH 9.8 was added to detect streptavidin-alkaline phosphatase, and color read when the highest wells (no inhibitor) had an O.D. at 405 nm of 1.5–2.0.

Binding is expressed as "% of No Addition Control." That is, in some wells, no inhibitor was present, and the binding in these wells represents the maximum (100%) binding.

Figure 6:
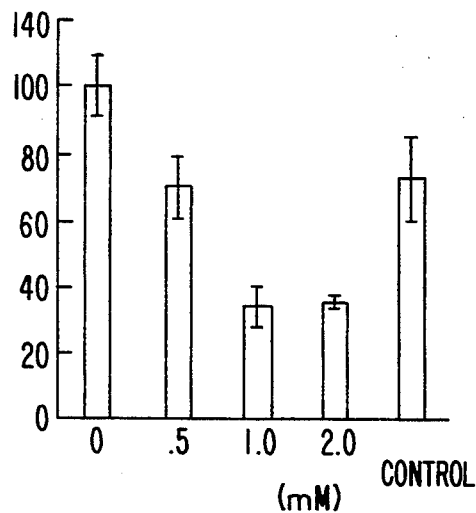
FIGS. 6, 7 and 8 are respectively graphs showing the ability of a multivalent derivative of sennoside A to inhibit the binding of SLE$^x$ to E-selectin, L-selectin and P-selectin.
Figure 7:
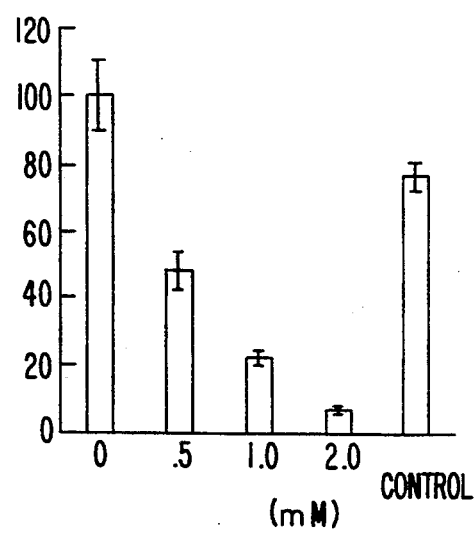
Figure 8:
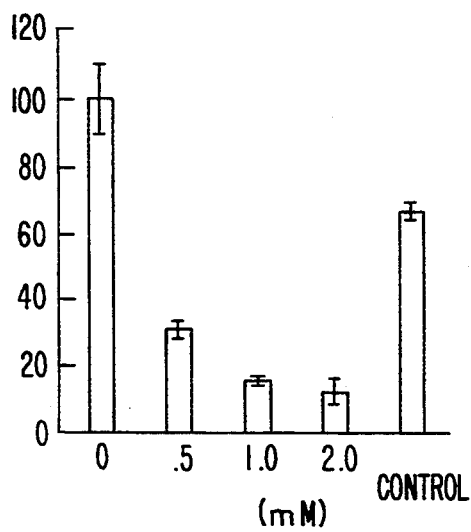

FIGS. 6, 7 and 8 show the results. Sennoside B inhibited P-(FIG. 8), L-(FIG. 7), and E-(FIG. 6), selectin binding to sLex, with P-selectin the most inhibited. The NaHCO3 controls showed inhibition as well; however, the inhibition observed with the controls was always less than the inhibition observed at high concentrations of selenoside B.

Based on the foregoing results it is clear that multivalent anthraquinone derivatives inhibit selectin binding to sLex.

The instant invention is shown and described herein in what is considered to be the most practical and preferred embodiments. Further, it is recognized that departures may be made therefrom which are within the scope of the invention, and that obvious modifications will occur to one skilled in the art upon reading this disclosure. Publications listed herein are incorporated herein by reference to disclose specific procedures on how to make, and/or use the invention.

What is claimed is:

1. A compound comprising the following structural formula I:

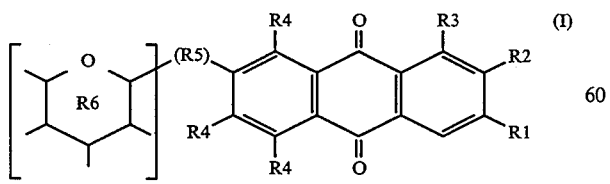

R1=OH, O-alkyl wherein the alkyl contains 1 to 6 carbon atoms, or O-linker wherein the linker group is an alkyl containing 1 to 12 carbon atoms or a heteroalkyl containing 1 to 12 atoms which contains heteroatoms selected from the group consisting of S, N and O;

R2=R—COOH, or CH2—O—CO2H, CH2O—R—CO2H, OCH2CO2H, O—R—O—SO3, O—R—O—PO3, or O—R—CO2H wherein R is an alkyl containing 1 to 6 carbon atoms;

R3=H, an alkyl containing 1 to 6 carbon atoms or a heteroalkyl containing 1 to 6 atoms with the heteroatom being selected from the group consisting of N, S and O;

R4 OH, or O—R' wherein R' is an alkyl containing 1 to 6 carbon atoms or a heteroalkyl containing 1 to 6 atoms with the heteroatom being selected from the group consisting of S and N;

R5=—(CH2)$_n$— wherein n is an integer of from 1 to 12 and the —(CH2)$_n$— group may be further attached to a heteroatom selected from the group consisting of N, S and O; and R6=Hexose or a hexNAc, or a disaccharide linked by either α- or β-linkage to R5 through an —O— linker or a linking group which includes as a base atom chain comprised of atoms selected from the group consisting of C, N and S, and pharmaceutically acceptable salts and multivalent derivatives of a compound of formula I.

2. A method of treating an animal for inflammation comprising administering to an animal in need thereof a therapeutically effective amount of a compound having the following structural formula I:

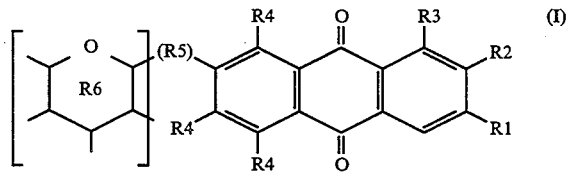

R1=OH, O-alkyl wherein the alkyl contains 1 to 6 carbon atoms, or O-linker wherein the linker group is an alkyl containing 1 to 12 carbon atoms or a heteroalkyl containing 1 to 12 atoms which contains heteroatoms selected from the group consisting of S, N and O;

R2=R—COOH, or CH2—O—CO2H, CH2O—R—CO2H, OCH2CO2H, O—R—O—SO3, O—R—O—PO3, or O—R—CO2H wherein R is an alkyl containing 1 to 6 carbon atoms;

R3=H, an alkyl containing 1 to 6 carbon atoms or a heteroalkyl containing 1 to 6 atoms with the heteroatom being selected from the group consisting of N, S and O;

R4=OH, or O—R' wherein R' is an alkyl containing 1 to 6 carbon atoms or a heteroalkyl containing 1 to 6 atoms with the heteroatom being selected from the group consisting of S and N;

R5=—(CH2)$_n$— wherein n is an integer of from 1 to 12 and the —(CH2)$_n$— group may be further attached to a heteroatom selected from the group consisting of N, S and O; and R6=Hexose or a hexNAc, or a disaccharide linked by either α- or β-linkage to R5 through an —O— linker or a linking group which includes as a base atom chain comprised of atoms selected from the group consisting of C, N and S, and pharmaceutically acceptable salts and multivalent derivatives of a compound of formula I.

3. The method of claim 2, wherein the animal is a human.

4. The method of claim 3, wherein the compound is administered via a route selected from the group consisting of intravenously, orally, transdermally and by inhalation.

5. The compound of claim 1, wherein
$R^1 = $ —OH
$R^2 = $ —COOH
$R^3 = $ H
$R^4 = $ OH 6. A mixture of compounds comprised of more than one of the compounds of formula I claimed in claim 1.

7. A conjugate comprising the compound of claim 1 covalently linked via the $R^1$ position to a pharmaceutically active drug.

8. The conjugate of claim 7, wherein the drug is an anti-inflammatory nonsteroidal drug.

9. The compound of claim 1, wherein the compound is a multivalent compound.

10. The compound of claim 9, wherein the compound is a multivalent derivative of sennoside A or sennoside B.

11. A pharmaceutical formulation comprising a compound of claim 1 and a pharmaceutically acceptable excipient carrier.

12. The formulation of claim 11, wherein
$R^1 = $ —OH
$R^2 = $ —COOH
$R^3 = $ H
$R^4 = $ OH 13. The formulation of claim 12, wherein the compound is a multivalent derivative of sennoside A or sennoside B.

14. An assay test material for determining the presence of ELAM-1 in a sample comprising:
a substrate the surface of which has bound thereto a ligand comprising the formula:

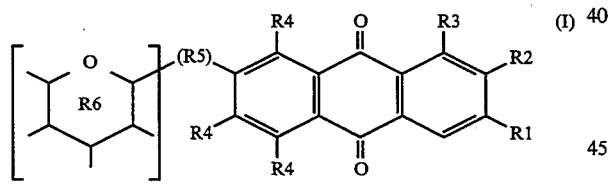

R1 = OH, O-alkyl wherein the alkyl contains 1 to 6 carbon atoms, or O-linker wherein the linker group is an alkyl containing 1 to 12 carbon atoms or a heteroalkyl containing 1 to 12 atoms which contains heteroatoms selected from the group consisting of S, N and O;
R2 = R—COOH, or CH$_2$—O—CO$_2$H, CH$_2$O—R—CO$_2$H, OCH$_2$CO$_2$H, O—R—O—SO$_3$, O—R—O—PO$_3$, or O—R—CO$_2$H wherein R is an alkyl containing 1 to 6 carbon atoms;
R3 = H, an alkyl containing 1 to 6 carbon atoms or a heteroalkyl containing 1 to 6 atoms with the heteroatom being selected from the group consisting of N, S and O;
R4 = OH, or O—R' wherein R' is an alkyl containing 1 to 6 carbon atoms or a heteroalkyl containing 1 to 6 atoms with the heteroatom being selected from the group consisting of S and N;
R5 = —(CH$_2$)$_n$— wherein n is an integer of from 1 to 12 and the —(CH$_2$)$_n$— group may be further attached to a heteroatom selected from the group consisting of N, S and O; and
R6 = Hexose or a hexNAc, or a disaccharide linked by either α- or β-linkage to R5 through an —O— linker or a linking group which includes as a base atom chain comprised of atoms selected from the group consisting of C, N and S, and
pharmaceutically acceptable salts and multivalent derivatives of a compound of formula I.

15. A method of assaying for the presence of an E-, L- or P-selectin in a sample, comprising the steps of:
providing a compound of claim 1 adhered to the surface of a substrate;
contacting the sample with the substrate surface; and
determining the presence of conjugates formed due to binding of a compound of formula I to an E-, L- or P-selectin in the sample.

16. A method of determining a site of inflammation in a patient, comprising the steps of:
administering to a patient a compound of claim 1 attached to a detectable label;
allowing the labeled compound sufficient time to circulate in the patient and attach to an E-, L- or P-selectin in the patient; and
detecting the label and its location in the patient and thereby determining the site of inflammation.

17. A method of assaying molecules for their ability to adhere to E-, L- or P-selectins comprising the steps of:
adhering molecules of claim 1 to a substrate surface;
contacting the molecules with labeled recombinant cells expressing high levels of an E-, L- or P-selectin for sufficient time to allow the cells to adhere to the molecules;
applying centrifugal force to the substrate in such a manner as to separate away cells which do not adhere to the molecules of formula I; and
detecting where the cells are bound to the compounds of formula I and thereby deducing the ability of such compounds to adhere to an E-, L- or P-selectin.

* * * * *